United States Patent
Kaji et al.

(10) Patent No.: US 9,301,692 B2
(45) Date of Patent: Apr. 5, 2016

(54) DENTAL OPTICAL SCANNING DEVICE AND DENTAL OPTICAL SCANNING/DIAGNOSING TOOL

(71) Applicant: J. Morita Manufacturing Corporation, Kyoto (JP)

(72) Inventors: Ryosuke Kaji, Kyoto (JP); Masayuki Sano, Kyoto (JP); Naotaro Nakata, Kyoto (JP); Mikinori Nishimura, Kyoto (JP); Shozo Nakayama, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 3 days.

(21) Appl. No.: 13/915,061

(22) Filed: Jun. 11, 2013

(65) Prior Publication Data

US 2013/0330686 A1 Dec. 12, 2013

(30) Foreign Application Priority Data

Jun. 11, 2012 (JP) ................................. 2012-131968

(51) Int. Cl.
*G01N 21/00* (2006.01)
*A61B 5/00* (2006.01)
*A61B 1/247* (2006.01)
*A61B 5/107* (2006.01)

(52) U.S. Cl.
CPC .............. *A61B 5/0088* (2013.01); *A61B 1/247* (2013.01); *A61B 5/0066* (2013.01); *A61B 5/1077* (2013.01); *A61B 5/742* (2013.01); *A61B 2562/0233* (2013.01)

(58) Field of Classification Search
CPC ............. G01B 9/02029; G01B 9/0203; G01B 9/0205; G01B 9/02054; G01B 9/02091
USPC .................................................... 356/479, 497
See application file for complete search history.

(56) References Cited

U.S. PATENT DOCUMENTS

| 2006/0158655 | A1* | 7/2006 | Everett et al. | 356/479 |
| 2007/0064238 | A1* | 3/2007 | Fujita | 356/479 |
| 2007/0076213 | A1* | 4/2007 | Kato | 356/479 |
| 2010/0296098 | A1* | 11/2010 | Bonnema et al. | 356/450 |

FOREIGN PATENT DOCUMENTS

| DE | 102009001086 A1 | 9/2010 |
| JP | 05-130995 | 5/1993 |
| JP | 2004-344260 A | 12/2004 |

(Continued)

OTHER PUBLICATIONS

B.T. Amaechi et al.: Application of Optical Coherence Tomography for Imaging and Assessment of Early Dental Caries Lesions. In: Laser Physics, vol. 13, No. 5, 2003, S. 703-710 (8 pages).

(Continued)

*Primary Examiner* — Jonathan Hansen
(74) *Attorney, Agent, or Firm* — Osha Liang LLP

(57) ABSTRACT

An OCT measuring mechanism for acquiring the optical coherence tomography information and a surface shape measuring mechanism for acquiring the three-dimensional shape information share a display device, a control device, a light source, a scanning mirror, a light transmission/receiving path and an entering/exiting opening. The scanning mirror, the light transmission/receiving path, the entering/exiting opening are included in a handpiece operable to make a diagnosis on a diagnostic target site.

11 Claims, 9 Drawing Sheets

(56) References Cited

FOREIGN PATENT DOCUMENTS

| | | | |
|---|---|---|---|
| JP | 2005-531346 | A | 10/2005 |
| JP | 2006-525066 | A | 11/2006 |
| JP | 2008-058138 | A | 3/2008 |
| JP | 2010-509993 | A | 4/2010 |
| JP | 2011529567 | A | 12/2011 |

OTHER PUBLICATIONS

M. Rominu et al.: Adhesive Improvement in Optical Coherence Tomography Combined with Confocal Microscopy for Class V Cavities Investigations. In: Proc. of SPIE, vol. 7626, 2010, 76260Y-1 bis 76260Y-8 (8 pages).

* cited by examiner

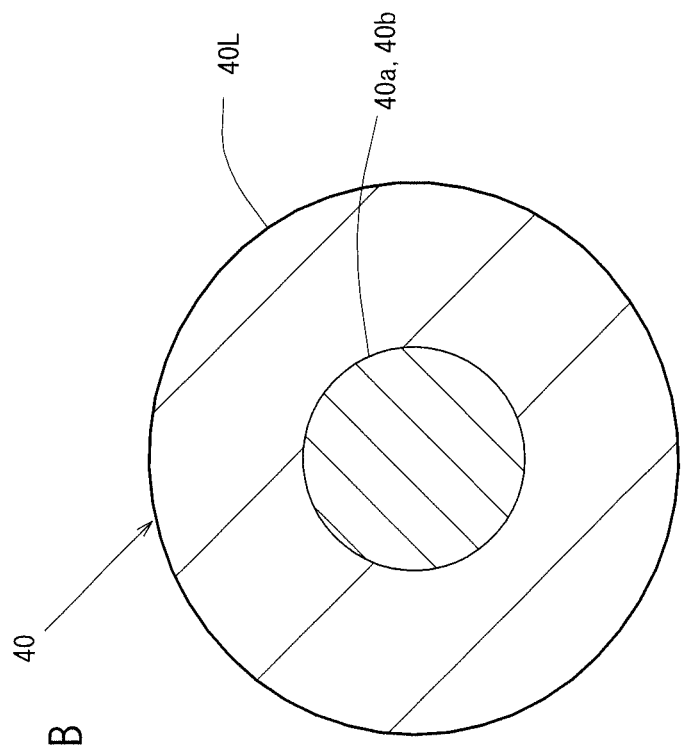
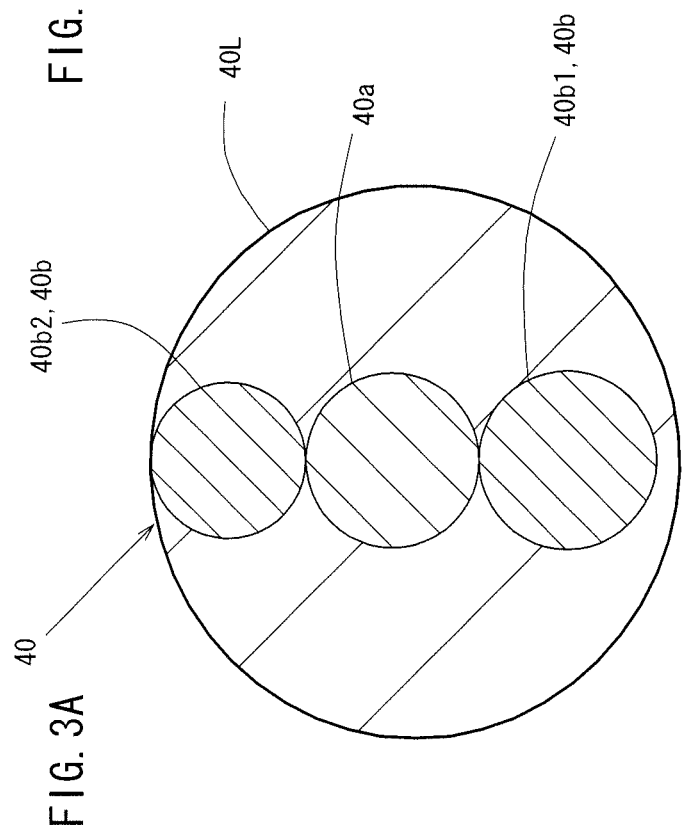

DENTAL OPTICAL SCANNING DEVICE AND DENTAL OPTICAL SCANNING/DIAGNOSING TOOL

BACKGROUND OF THE INVENTION

1. Field of the Invention

The present invention relates a dental optical measuring device and a dental optical measuring/diagnosing tool usable, for example, for making a diagnosis on an oral cavity.

2. Description of the Prior Art

Along with the advancement of diagnostic techniques, it is now desired to acquire detailed and accurate information on a diagnostic target site more than ever before.

For example, Patent Document 1 proposes a dental tomographic image display system, by which a tomographic image of a tooth and the gum is acquired by use of optical coherence tomography.

The dental tomographic image display system described in Patent Document 1 scans a certain range with light of an oscillation wavelength, allows the light to be incident on a probe, performs scanning and irradiation with signal light by use of a coherent optical meter and an optical path scanning change section provided in the probe, and causes interference of scattered light from a detection target and reference light in the probe to acquire coherent light. The dental tomographic image display system is structured such that the coherent signal is processed with Fourier transformation to acquire an image signal in a depth direction, and also such that the image is located based on a scanning direction to acquire two-dimensional tomographic image from the optical coherence tomography information.

As another method, Patent Document 2 proposes a dental three-dimensional camera for recording a surface structure of a diagnostic target site by use of triangulation.

The optical coherence tomography information acquired by the tomographic image display system as disclosed in Patent Document 1 and the three-dimensional shape information acquired by the three-dimensional camera as disclosed in Patent Document 2 are different from each other. Therefore, an appropriate device among diagnostic devices used for the respective methods needs to be used to acquire information appropriate for a specific part of the diagnostic target site or the content of diagnosis.

However, these diagnostic devices are independent from each other. In order to acquire optical coherence tomography information and three-dimensional shape information, large-scale facilities are necessary. In addition, it is necessary to first acquire information on the diagnostic target site by either an optical coherence tomography information acquisition device such as a tomographic image display system or a three-dimensional shape information acquisition device such as a three-dimensional camera, and then replace the device to acquire the other information.

PRIOR ART DOCUMENT

Patent Document

Patent Document 1: Japanese Laid-Open Patent Publication No. 2008-058138
Patent Document 2: PCT Japanese National Phase Laid-Open Patent Publication No. 2006-525066

SUMMARY OF THE INVENTION

Problems to be Solved by the Invention

In light of the above-described problem, the present invention has an object of providing a dental optical measuring device and a dental optical measuring/diagnosing tool capable of acquiring both of optical coherence tomography information and three-dimensional shape information with a compact structure with no need of device replacement.

Solutions for the Problems

The present invention is directed to a dental optical measuring device, including an optical three-dimensional surface measuring system structure including a measurement result display section for displaying at least a measurement result, a measurement control section for controlling a measurement, a measuring light emitting section for emitting measuring light, a scanning mirror usable for scanning performed with the measuring light, an exiting opening through which the measuring light is directed toward a measurement target, a light transmission path for guiding the measuring light to the exiting opening, an entering opening on which the measuring light directed from the exiting opening is incident after being scattered by the measurement target, a light receiving path for guiding the scattered light incident on the entering opening, and a light receiving section for receiving the scattered light guided by the light receiving path; and an optical coherence tomography measuring system structure including a measurement result display section for displaying at least a measurement result, a measurement control section for controlling a measurement, a measuring light emitting section for emitting measuring light, a light dividing section for dividing the measuring light into measuring light and reference light, a scanning mirror usable for scanning performed with the measuring light, an exiting opening through which the measuring light is directed toward the measurement target, a light transmission path for guiding the measuring light to the exiting opening, an entering opening on which the measuring light directed from the exiting opening is incident after being scattered by the measurement target, a light receiving path for guiding the scattered light incident on the entering opening, a reflective mirror for reflecting the reference light obtained as a result of the division performed by the light dividing section, a light interfering section for causing interference of the reflected reference light reflected by the reflective mirror and the scattered light, and a coherent light receiving section for receiving coherent light generated by the interference performed by the light interfering section. The optical three-dimensional surface measuring system structure and the optical coherence tomography measuring system structure share at least one of the measurement result display section, the measurement control section, the measuring light emitting section, the scanning mirror, the light transmission path, the exiting opening, the entering opening and the light receiving path; and at least the scanning mirror, the light transmission path, the exiting opening, the entering opening and the light receiving path are included in a diagnosing tool operable to make a diagnosis on the measurement target.

The optical three-dimensional surface measuring system structure may be formed of a device for measuring the shape of the diagnostic target site in a contactless manner by, for example, a triangulation method such as a spot light projection method (light probe method), a light section method (slit light projection method), a pattern light projection method (space coding method), a phase shift method or the like, a confocal method, a focal point method or the like.

The optical coherence tomography measuring system structure may be formed of, for example, an OCT (Optical Coherence Tomography) device of TD-OCT (time domain OCT), SD-OCT (spectral domain OCT), SS-OCT (swept source OCT) or the like.

The diagnosing tool is called a "handpiece" and performs, for example, impression taking by inserting a part thereof into the oral cavity.

According to this invention, a device for acquiring both of optical coherence tomography information and three-dimensional shape information with a compact structure with no need of device replacement can be provided.

This will be described in more detail. At least one of the measurement result display section, the measurement control section, the measuring light emitting section, the scanning mirror, the light transmission path, the exiting opening, the entering opening and the light receiving path is shared by the optical three-dimensional surface measuring system structure and the optical coherence tomography measuring system structure. Owing to this, as compared with the case where a device for acquiring the optical coherence tomography information and a device for acquiring the three-dimensional shape information are separately prepared, the dental optical measuring device can be more compact.

In addition, at least one of the scanning mirror, the light transmission path, the exiting opening, the entering opening and the light receiving path are included in the diagnosing tool operable to make a diagnosis on the measurement target. Owing to this, both of the optical coherence tomography information and the three-dimensional shape information can be acquired by one diagnosing tool with no need of device replacement.

Therefore, one dental optical measuring device can acquire inside information on the diagnostic target site based on the optical coherence tomography information and the surface information on the diagnostic target site based on the three-dimensional surface shape information. These pieces of information are synthesized and complemented by each other. As a result, highly precise three-dimensional volume data including inside tomography of the oral cavity can be acquired. The highly precise three-dimensional volume data is usable as impression data for producing a prosthetic appliance for dental treatment, and also usable for a highly precise diagnosis on initial dental caries of the surface or the inside of the tooth, root fracture or the like. The highly precise three-dimensional volume data is also usable as data for designing for embedding an implant.

In an embodiment of the invention, the optical three-dimensional surface measuring system structure and the optical coherence tomography measuring system structure may share the scanning mirror, the light transmission path, the exiting opening, the entering opening and the light receiving path.

According to this invention, the optical three-dimensional surface measuring system structure and the optical coherence tomography measuring system structure share a plurality of elements. Therefore, the dental optical measuring device can be more compact.

In an embodiment of the invention, the light transmission path and the light receiving path may include a lens system light guide path for guiding the measuring light to the exiting opening and for guiding the scattered light from the entering opening.

According to this invention, the optical paths can guide light more stably as compared with an optical path formed of, for example, a light guide or the like. The refractive index, the light guide ratio and the like of the lens can be set to provide a prescribed level of performance.

In an embodiment of the invention, the light transmission path and the light receiving path of the optical coherence tomography measuring system structure may be located on an optical axis of the lens system light guide path; and the light transmission path and the light receiving path of the optical three-dimensional surface measuring system structure may be located at an eccentric position which is eccentric from the optical axis of the lens system light guide path.

According to this invention, the light transmission path and the light receiving path of the optical three-dimensional surface measuring system structure for performing a measurement by triangulation, and the light transmission path and the light receiving path of the optical coherence tomography measuring system structure, can be established while the precision of both thereof is maintained with no mutual interference in the same lens system light guide path.

In an embodiment of the invention, the measuring light emitting section of the optical three-dimensional surface measuring system structure and the measuring light emitting section of the optical coherence tomography measuring system structure may be separately provided.

According to this invention, the measuring light suitable for each type of measurement can be emitted for the measurement. Since the measuring light emitting section of the optical three-dimensional surface measuring system structure and the measuring light emitting section of the optical coherence tomography measuring system structure are separately provided, the measuring light can be emitted from the measuring emitting sections at the same time. Therefore, the optical coherence tomography information and the three-dimensional shape information can be acquired at the same time.

In an embodiment of the invention, the light dividing section and the light interfering section may be integrally provided as a light dividing/interfering section for dividing the measuring light into the measuring light and the reference light and causing interference of the reflected reference light and the scattered light to generate coherent light.

The light dividing/interfering section can be formed of a tool called a "2×2 fiber coupler".

According to this invention, the dental optical measuring device including the light dividing/interfering section can be more compact as compared with the case where the light dividing section for dividing the measuring light into the measuring light and the reference light, and the light interfering section for causing interference of the reflected reference light and the scattered light to generate the coherent light, are separately provided.

In an embodiment of the invention, the scanning mirror, the light dividing/interfering section, the light transmission path, the exiting opening, the light receiving path, the reflective mirror, the coherent light receiving section and the entering opening of the optical coherence tomography measuring system structure may be included in the diagnosing tool.

According to this invention, the measuring light is divided by the light dividing/interfering section and is directed toward the diagnostic target site via the light transmission path and the exiting opening. The measuring light is also reflected by the reflective mirror. The scattered light incident on the entering opening after being scattered by the diagnostic target site and the reflected reference light reflected by the reflective mirror are used to generate the coherent light by the light dividing/interfering section, and the coherent light is received by the coherent light receiving section. Thus, the optical coherence tomography information can be acquired.

Effect of the Invention

According to the present invention, a dental optical measuring device and a dental optical measuring/diagnosing tool capable of acquiring both of optical coherence tomography information and three-dimensional shape information with a compact structure with no need of device replacement can be provided.

BRIEF DESCRIPTION OF DRAWINGS

FIGS. 3A and 3B schematically show a light transmission/receiving path.

DESCRIPTION OF THE PREFERRED EMBODIMENTS

Hereinafter, an embodiment of the present invention will be described with reference to the drawings.

Figure 1:
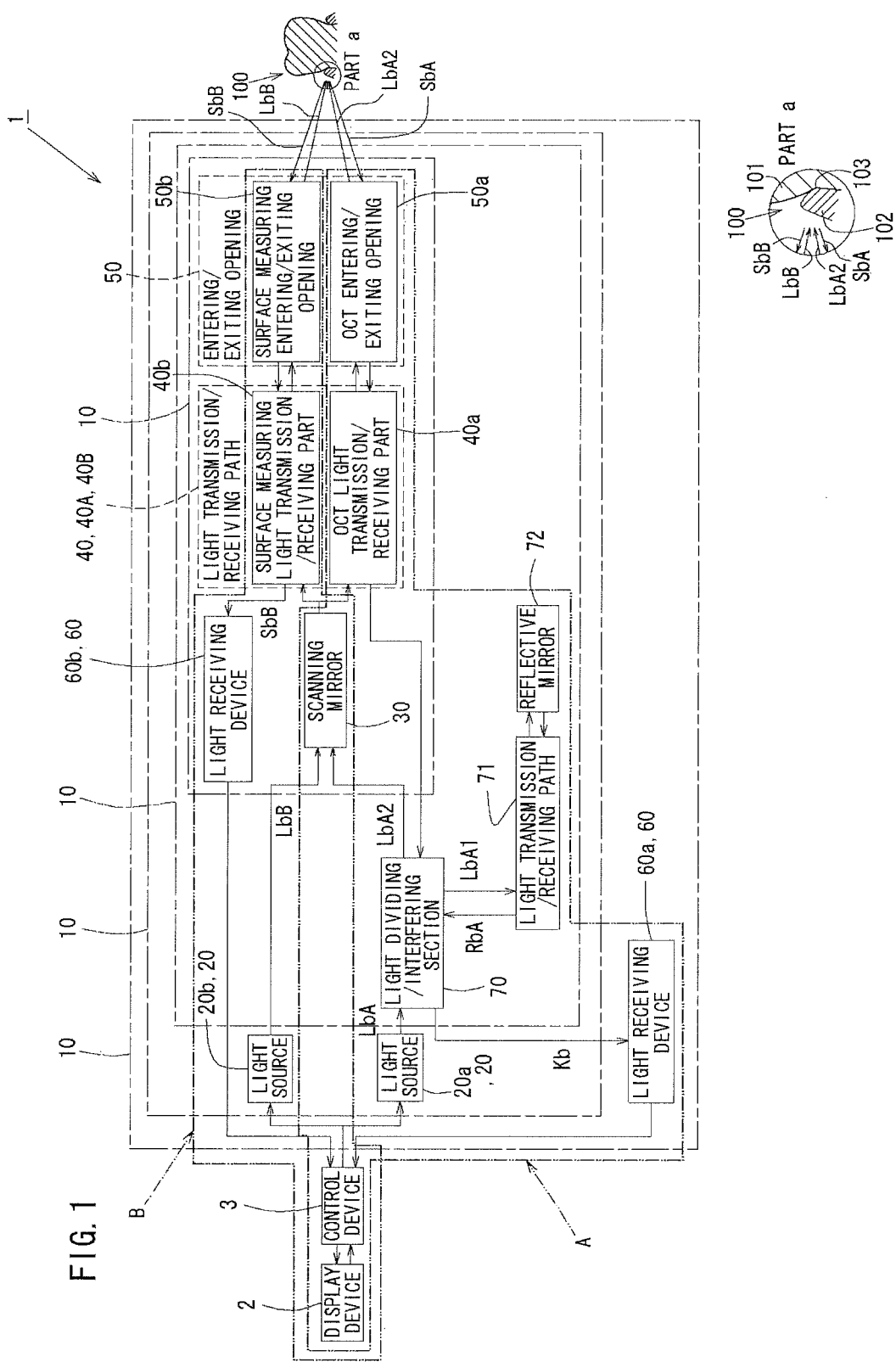
FIG. 1 is a schematic structural view of a dental optical measuring device.
Figure 2:
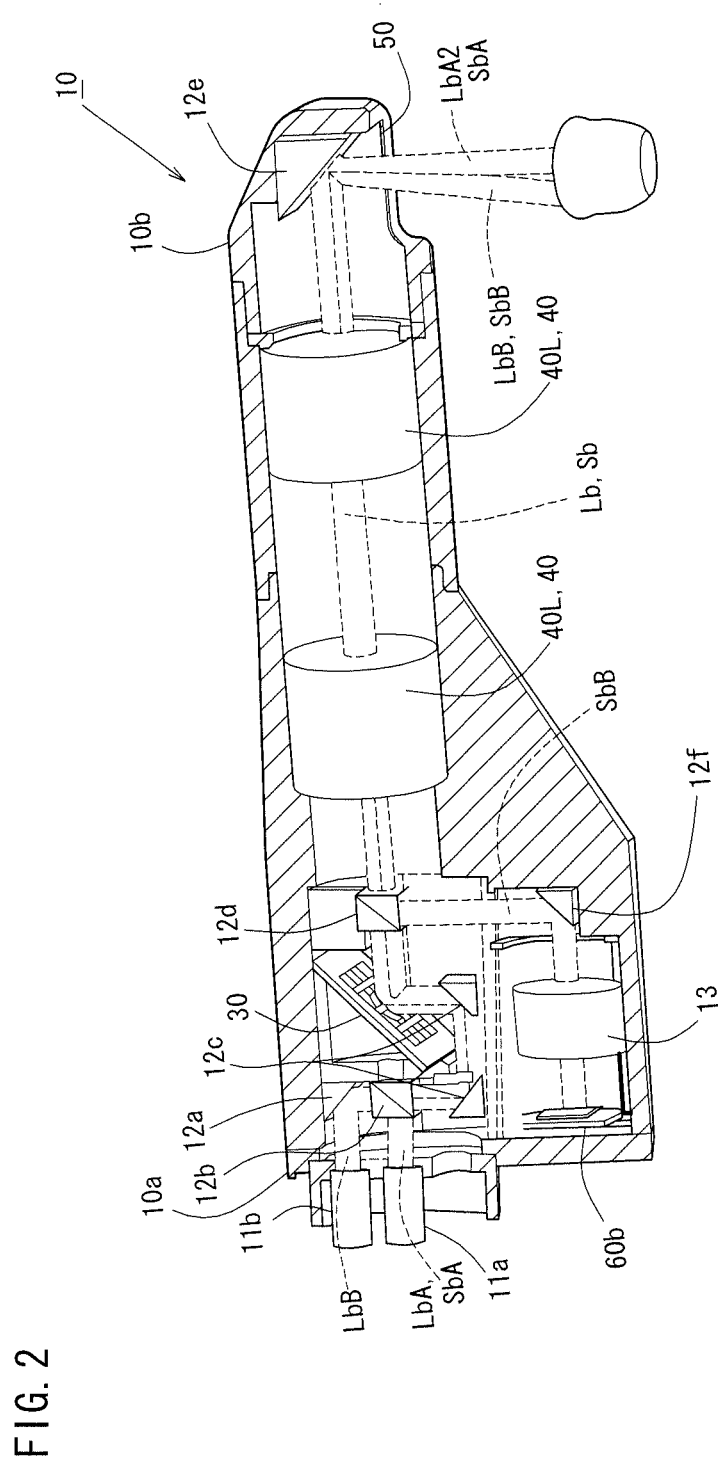
FIG. 2 is a schematic cross-sectional view of a handpiece.
Figure 4:
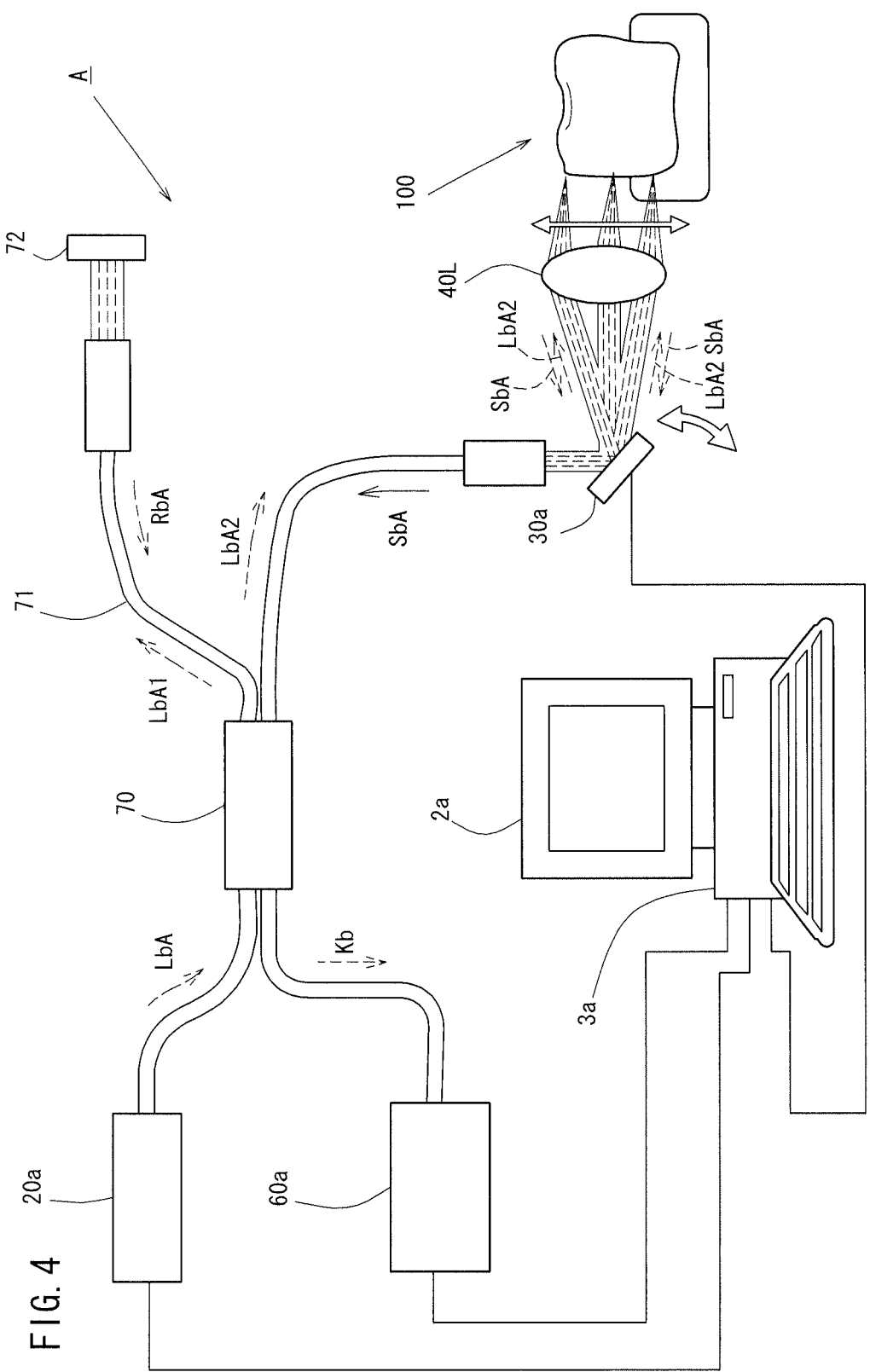
FIG. 4 is a schematic structural view of an OCT measuring mechanism.

FIG. 1 is a schematic structural view of a dental optical measuring device 1. FIG. 2 is a schematic cross-sectional view of a handpiece 10. FIGS. 3A and 3B schematically show a light transmission/receiving path 40 of the handpiece 10. FIG. 4 is a schematic structural view of an OCT measuring mechanism A. FIGS. 5A-5D schematically show a structure of a surface shape measuring mechanism B.

The dental optical measuring device 1 is a diagnostic device capable of acquiring highly precise three-dimensional volume data which includes an internal tomography of a diagnostic target site 100 and is usable for, for example, impression taking. As shown in, for example, enlarged part "a" of FIG. 1, impression taking of a margin 103 which is cervix dentis of a tooth 101 in the diagnostic target site 100 and is covered with gum 102 can be performed with no exclusion of the gum 102. Needless to say, a part of the tooth 101 which is not covered with the gum 102, as well as the margin 103, may be set as the diagnostic target site 100 and precise three-dimensional volume data thereof may be acquired.

For acquiring such data, the dental optical measuring device 1 includes an OCT measuring mechanism A for acquiring internal information of the diagnostic target site 100 by OCT and a surface shape measuring mechanism B for acquiring three-dimensional shape information of a surface of the diagnostic target site 100 by a surface measuring method such as triangulation or the like.

This will be described in more detail. As shown in FIG. 4, the OCT measuring mechanism A for acquiring internal information of the diagnostic target site 100 by OCT includes a control device 3a connected to a display device 2a formed of an output screen, a light source 20a for emitting OCT measuring light LbA, and a light dividing/interfering section 70. The light dividing/interfering section 70 divides the OCT measuring light LbA emitted by the light source 20a into reference light LbA1 and irradiation measuring light LbA2, and causes interference of scattered light SbA, which is obtained as a result of the irradiation measuring light LbA2 directed toward the diagnostic target site 100 being scattered rearward, and reflected light RbA described later to acquire coherent light Kb. The light dividing/interfering section 70 is formed of, for example, a 2×2 fiber coupler. The OCT measuring mechanism A further includes a scanning mirror 30a for directing the irradiation measuring light LbA2 such that objective lenses 40L located in an OCT light transmission/receiving part 40a are scanned with the irradiation measuring light LbA2, a reflective mirror 72 for reflecting the reference light LbA1, obtained as a result of the division performed by the light dividing/interfering section 70, as the reflected light RbA, a light transmission/receiving path 71 for guiding the reference light LbA1 and the reflected light RbA between the light dividing/interfering section 70 and the reflective mirror 72, and a light receiving device 60a for converting the coherent light Kb, obtained as a result of the interference performed by the light dividing/interfering section 70, into an electric signal. The light receiving device 60a is formed of a photodiode or the like.

The OCT measuring mechanism A structured as described above operates as follows. The OCT measuring light LbA directed from the light source 20a is divided by the light dividing/interfering section 70 into the irradiation measuring light LbA2 and the reference light LbA1. The irradiation measuring light LbA2 is reflected by the diagnostic target site 100 to become the scattered light SbA, and the reference light LbA1 is reflected by the reflective mirror 72 to become the reflected light RbA. The light dividing/interfering section 70 receives the scattered light SbA and the reflected light RbA to obtain the coherent light Kb.

The control device 3a detects the intensity of the coherent light Kb obtained by the interference of the reflected light RbA and the scattered light SbA, and thus acquires optical coherence tomography information of the diagnostic target site 100.

Such an operation is performed for each of various parts of the diagnostic target site 100, which is a target of information detection, while the diagnostic target site 100 is scanned with light by use of the scanning mirror 30a such that the part thereof irradiated with the light is varied. Thus, the optical coherence tomography information on each part is acquired. As a result, the optical coherence tomography information containing a tissue profile at a certain depth from the surface of the diagnostic target site 100 is acquired. For example, an image of a surface shape of the tooth 101 or the gum 102, and also tissue information of the inside of the tooth 101 or the gum 102, are acquired. Especially when the cervix dentis, which is also called the margin, is covered with the gum 102, tissue information of the cervix dentis of the tooth 101 is acquired. Such optical coherence tomography information is subjected to image processing, and thus inside information of the diagnostic target site 100 is acquired.

The surface shape measuring mechanism B acquires the three-dimensional shape information of the surface of the diagnostic target site 100 by a surface measuring method such as triangulation or the like, and forms the three-dimensional shape information into an image. As shown in FIGS. 5A-5D, the surface shape measuring mechanism B include a control device 3b connected to a display device 2b formed of an output screen, a light source 20b for emitting surface measuring light LbB, a scanning mirror 30b for directing the surface measuring light LbB emitted by the light source 20b such that the objective lenses 40L located in a surface measuring light transmission/receiving part 40b are scanned with the surface measuring light LbB, and a light receiving device 60b for receiving scattered light SbB, obtained as a result of the surface measuring light LbB directed toward the diagnostic target site 100 being scattered rearward by the surface of the diagnostic target site, and converting the scattered light SbB into an electric signal. The light receiving device 60b is formed of a CCD camera or the like.

Figure 5A:
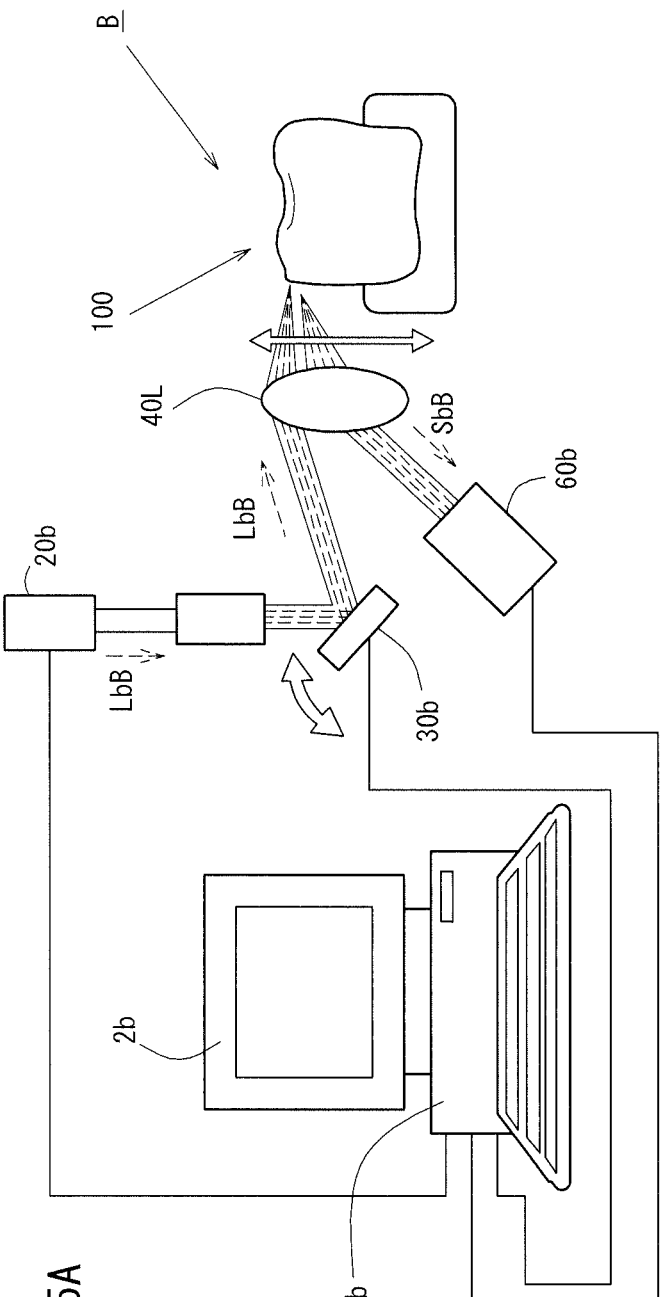
FIGS. 5A-5D schematically show a structure of a surface shape measuring mechanism.
Figure 5D:
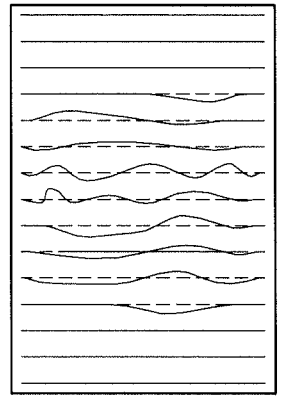
Figure 5C:
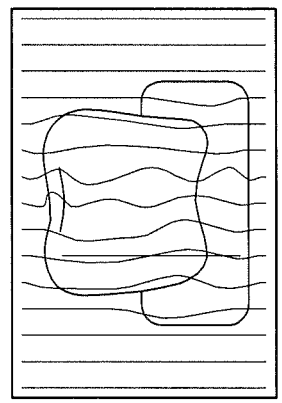
Figure 5B:
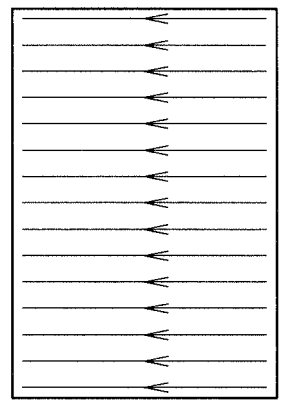

The surface shape measuring mechanism B structured as described above operates as follows. FIG. 5B shows a state in which the surface measuring light LbB is directed by triangulation. As shown in FIG. 5B, the diagnostic target site 100 is scanned while being irradiated with the surface measuring light LbB. The light receiving device 60b receives the scattered light SbB, obtained as a result of the surface measuring light LbB directed toward the diagnostic target site 100 being scattered rearward, in an oblique direction (see FIG. 5C), and thus can measure the surface shape of the diagnostic target site 100 and form an image thereof (see FIG. 5D).

The dental optical measuring device 1 includes the OCT measuring mechanism A capable of acquiring inside information of the diagnostic target site 100 and the surface shape measuring mechanism B capable of acquiring three-dimensional shape information of the surface of the diagnostic target site 100. Thus, the dental optical measuring device 1 includes the display device 2, the control device 3, the light sources 20, the scanning mirror 30, the light transmission/receiving path 40, an entering/exiting opening 50, the light receiving device 60, the light dividing/interfering section 70, the light transmission/receiving path 71, and the reflective mirror 72. The scanning mirror 30, the light transmission/receiving path 40, and the entering/exiting opening 50 are included in the handpiece 10.

This will be described in more detail. The display device 2 is connected to the control device 3 described later, and is controlled by the control device 3 to display an operation menu for, and measurement results provided by, the dental optical measuring device 1. The display device 2 also receives input operations.

The control device 3 is connected to the display device 2, the light source 20 described later, the scanning mirror 30, and the light receiving device 60, and controls these elements. The control device 3 includes a storage section, a CPU and the like.

The light sources (20a, 20b) are controlled by the control section 3 to emit laser light suitable to each type of measurement.

The scanning mirror 30 reflects light directed thereto and changes a guiding direction in which the light is guided. The scanning mirror 30 is controlled by the control device 3 to adjust the orientation thereof.

The light transmission/receiving path 40 includes the objective lenses 40L capable of guiding light arranged in a longitudinal direction of the handpiece 10.

The entering/exiting opening 50 allows light to enter, or exit from, the dental optical measuring device 1.

In the dental optical measuring device 1, the display device 2, the control device 3, the scanning mirror 30, the light transmission/receiving path 40 and the entering/exiting opening 50 each act as the respective elements of the OCT measuring mechanism A and the surface shape measuring mechanism B. In other words, in the dental optical measuring device 1, the display device 2, the control device 3, the scanning mirror 30, the light transmission/receiving path 40 and the entering/exiting opening 50 are shared by the OCT measuring mechanism A and the surface shape measuring mechanism B.

However, as described later in more detail, the light transmission/receiving path 40 shared by the OCT measuring mechanism A and the surface shape measuring mechanism B includes an OCT light transmission/receiving part 40a and a surface measuring light transmission/receiving part 40b which are different from each other in light introduction parts thereof. The entering/exiting opening 50 shared by the OCT measuring mechanism A and the surface shape measuring mechanism B includes an OCT entering/exiting opening 50a and a surface measuring entering/exiting opening 50b which are different from each other in light introduction parts thereof.

The light source 20 includes the light source 20a and 20b which are not shared by the OCT measuring mechanism A and the surface shape measuring mechanism B, and the light receiving devices 60 includes the light receiving devices 60a and 60b which are not shared by the OCT measuring mechanism A and the surface shape measuring mechanism B. The light dividing/interfering section 70, the light transmission/receiving path 71 and the reflective mirror 72 are included only in the OCT measuring mechanism A.

The length of an optical path from the light dividing/interfering section 70 to the reflective mirror 72 along which the reference light LbA1 is guided is set to be equal to the length of an optical path from the light dividing/interfering section 70 to the diagnostic target site 100 via the scanning mirror 30, the light transmission/receiving path 40 and the entering/exiting opening 50 along which the irradiation measuring light LbA2 is guided.

In the dental optical measuring device 1 structured as described above, as shown in FIG. 2, the handpiece 10 including the scanning mirror 30, the light transmission/receiving path 40 and the entering/exiting opening 50 is a diagnosing tool which is formed to be generally cylindrical. The handpiece 10 receives outgoing light Lb (LbA, LbB) incident on a rear end 10a (left in FIG. 2) thereof and directs the light Lb downward from a tip end 10b (right in FIG. 2) thereof, which is insertable into the oral cavity.

This will be described in more detail. The handpiece 10 includes introduction sections 11 (11a, 11b) located at the rear end 10a, a first mirror 12a, a beam combiner 12b, second mirrors 12c, the scanning mirror 30, a beam splitter 12d, the light transmission/receiving path 40, a third mirror 12e, the entering/exiting opening 50, a fourth mirror 12f, the light receiving device 60b, and a lens 13. The introduction sections 11 (11a, 11b) respectively introduce the irradiation measuring light LbA2, obtained as a result of the OCT measuring light LbA from the light source 20a in the OCT measuring mechanism A being divided by the light dividing/interfering section 70, and the surface measuring light LbB from the light source 20b in the surface shape measuring mechanism B. The first mirror 12a changes the guiding direction of the surface measuring light LbB introduced from the introduction section 11b. The beam combiner 12b changes the guiding direction of the irradiation measuring light LbA2 introduced from the introduction section 11a, and allows the surface measuring light LbB, the guiding direction of which has been changed by the first mirror 12a, to pass therethrough. The second mirrors 12c change the guiding direction of the outgoing light Lb (LbA2, LbB) such that the outgoing light Lb does not pass the scanning mirror 30 described later. The scanning mirror 30 adjusts the guiding direction of the outgoing light Lb. The beam splitter 12d allows the outgoing light Lb, the guiding direction of which has been changed by the adjustment performed by the scanning mirror 30, to pass therethrough, allows the scattered light SbA described later to pass therethrough, and changes the guiding direction of the scattered light SbB. The light transmission/receiving path 40 allows the outgoing light Lb and the scattered light Sb to be guided therethrough. The third mirror 12e changes the guiding direction of the outgoing light Lb, which has passed the light transmission/receiving path 40, such that the outgoing light Lb is directed toward the entering/exiting opening 50, and changes the guiding direction of the scattered light Sb incident on the entering/exiting opening 50 such that the scattered light Sb is directed toward the light transmission/receiving path 40. The entering/exiting opening 50 directs the outgoing light Lb toward the diagnostic target site 100, and allows the scattered light Sb scattered rearward by the diagnostic target site 100 to be incident on the handpiece 10. The fourth mirror 12*f* changes the guiding direction of the scattered light SbB, which has passed the light transmission/receiving path 40 from the tip end 10*b* toward the rear end 10*a* and had the guiding direction thereof changed by the beam splitter 12*d*, such that the scattered light SbB is directed toward the light receiving device 60*b* described later. The receiving device 60*b* receives the scattered light SbB which has passed the fourth mirror 12*f*, and is formed of a CMOS element or the like. The lens 13 is located between the fourth mirror 12*f* and the light receiving device 60*b*.

The scanning mirror 30 and the light receiving device 60*b* included in the handpiece 10 are connected to, and controlled by, the control device 3 (FIG. 1).

As shown in FIG. 3A, the irradiation measuring light LbA2 and the scattered light SbA pass the center or the vicinity thereof of the objective lenses 40L included in the light transmission/receiving path 40, and the surface measuring light LbB and the scattered light SbB pass positions eccentric from the center of the objective lenses 40L. An area including the center of the objective lenses 40 and the vicinity thereof through which the irradiation measuring light LbA2 and the scattered light SbA pass is labeled as the OCT light transmission/receiving part 40*a*, and the positions eccentric from the center of the objective lenses 40L through which the surface measuring light LbB and the scattered light SbB pass are labeled as the surface measuring light transmission/receiving parts 40*b* (40*b*1, 40*b*2).

According to an OCT measuring technique, the irradiation measuring light LbA2 going out from the OCT entering/exiting opening 50*a* and the scattered light SbA incident on the OCT entering/exiting opening 50*a* from the diagnostic target site 100 need to proceed through the same optical path. According to a triangulation technique, the surface measuring light LbB going out from the surface measuring entering/exiting opening 50*b* and the scattered light SbB incident on the surface measuring entering/exiting opening 50*b* from the diagnostic target site 100 need to pass optical paths having a triangulation angle of 2θ with respect to each other. θ is an angle made by an optical axis of the objective lenses 40L and the optical path of the surface measuring light LbB going out of the objective lenses 40L. Where the eccentric amount of the surface measuring light LbB with respect to the optical axis of the objective lenses 40L is s and the focal distance of the objective lenses 40L is f, tan θ=s/f.

A light guide path in the handpiece 10 structured as described above will be described.

The irradiation measuring light LbA2, obtained as a result of the OCT measuring light LbA emitted by the light source 20*a* being divided by the light dividing/interfering section 70 is introduced into the handpiece 10 from the introduction section 11*a*. Similarly, the surface measuring light LbB emitted by the light source 20*b* is introduced into the handpiece 10 from the introduction section 11*b*.

The surface measuring light LbB introduced from the introduction section 11*b* has the guiding direction thereof changed by the first mirror 12*a* and passes the beam combiner 12*b*. The irradiation measuring light LbA2 introduced from the introduction section 11*a* has the guiding direction thereof changed by the beam combiner 12*b*. The irradiation measuring light LbA2 and the surface measuring light LbB, which has passed the beam combiner 12*b*, have the guiding direction thereof changed by the second mirrors 12*c* so as to avoid the scanning mirror 30, and is guided to the scanning mirror 30.

The outgoing light Lb (LbA2, LbB) having the guiding direction thereof changed by the scanning mirror 30 controlled by the control device 3 passes the beam splitter 12*d* and then the light transmission/receiving path 40. In this case, the irradiation measuring light LbA2 passes the OCT light transmission/receiving part 40*a* of the light transmission/receiving path 40, and the surface measuring light LbB passes the surface measuring light transmission part 40*b*1 of the light transmission/receiving path 40.

The outgoing light Lb, which has passed the light transmission/receiving path 40, has the guiding direction thereof changed by the third mirror 12*e*, and goes out from the entering/exiting opening 50 toward the diagnostic target site 100. The outgoing light Lb, which has come out from the entering/exiting opening 50, is scattered rearward on a surface of, and inside of, the diagnostic target site 100. The scattered light Sb (SbA, SbB) is incident on the handpiece 10 from the entering/exiting opening 50. The scattered light Lb, which has been incident on the entering/exiting opening 50, has the guiding direction thereof changed by the third mirror 12*e* so as to be directed toward the light transmission/receiving path 40, and passes the light transmission/receiving path 40 from the tip end 10*b*. In this case, the scattered light SbA passes the OCT light transmission/receiving part 40*a* of the light transmission/receiving path 40, and the scattered light SbB passes the surface measuring light receiving part 40*b*2 of the light transmission/receiving path 40.

The scattered light SbB, which has passed the surface measuring light receiving part 40*b*2 of the light transmission/receiving path 40, has the guiding direction thereof changed by the beam splitter 12*d* and the fourth mirror 12*f* and passes the lens 13 to be directed toward the light receiving device 60*b*. The light receiving device 60*b*, which has received the scattered light SbB directed thereto, transmits the image information to the control device 3 as an electric signal.

The scattered light SbA, which has passed the OCT light transmission/receiving part 40*a* of the light transmission/receiving path 40, passes the beam splitter 12*d*, has the guiding direction thereof changed by the scanning mirror 30, and has the guiding direction thereof changed by the second mirrors 12*c* and the beam combiner 12*b* to be guided out of the handpiece 10 from the introduction section 11*a*.

While the orientation of the scanning mirror 30 is controlled to be changed by the control device 3 such that the outgoing light Lb passes the optical path as described above, the surface of the diagnostic target site 100 is scanned with the outgoing light Lb for a measurement.

As described above, the handpiece 10 is structured such that the scanning mirror 30, the light transmission/receiving path 40 and the entering/exiting opening 50 are shared by the OCT measuring mechanism A and the surface shape measuring mechanism B.

A method by which the dental optical measuring device 1 including the handpiece 10 structured as described above performs a measurement will be described.

First, when an operator makes an input to start the measurement on a menu screen displayed on the display device 2, the control device 3 controls the light sources 20 (20*a*, 20*b*) to emit outgoing light Lb.

The OCT measuring light LbA emitted by the light source 20*a* is guided to the light dividing/interfering section 70 and is divided by the light dividing/interfering section 70 into the reference light LbA1 and the irradiation measuring light LbA2. The irradiation measuring light LbA2 and the surface measuring light LbB are introduced into the handpiece 10 from the introduction sections 11. The reference light LbA obtained as a result of the division performed by the light dividing/interfering section 70 passes the light transmission/receiving path 71 and is directed toward the reflective mirror 72. The reflected light RbA obtained by the reference light LbA being reflected by the reflective mirror 72 passes the light transmission/receiving path 71 and is guided to the light dividing/interfering section 70.

As described above, the outgoing light lb introduced into the handpiece 10 passes the mirrors, the beam combiner and beam splitter 12, the scanning mirror 30, the light transmission/receiving path 40 and the entering/exiting opening 50, goes out toward the diagnostic target site 100, is scattered rearward on the surface of, and inside of, the diagnostic target site 100, and is incident on the handpiece 10 from the entering/exiting opening 50 as the scattered light Sb (SbA, SbB).

As described above, the scattered light SbB incident on the entering/exiting opening 50 passes the light transmission/receiving path 40, the mirrors, the beam combiner and beam splitter 12 and the lens 13 in the handpiece 10 and is directed toward the light receiving device 60b. The light receiving device 60b, which has received the scattered light SbB, converts the received scattered light SbB into an electric signal and transmits the electric signal to the control device 3.

The scattered light LbA incident on the entering/exiting opening 50 passes the light transmission/receiving path 40, the scanning mirror 30, the mirrors, and the beam combiner and beam splitter 12, is guided out from the handpiece 10 from the introduction section 11a, and is guided toward the light dividing/interfering section 70.

The scattered light SbA guided to the light dividing/interfering section 70, and the reflected light RbA reflected by the reflective mirror 72, which is located at a position away from the light dividing/interfering section 70 by a distance equal to the distance from the light dividing/interfering section 70 to the diagnostic target site 100, are used to generate the coherent light Kb by the light dividing/interfering section 70. The coherent light Kb is guided to the light receiving device 60a.

The light receiving device 60a, which has received the coherent light Kb, converts the intensity of the coherent light Kb into an electric signal and transmits the electric signal to the control device 3.

The surface of the diagnostic target site 100 is scanned with the outgoing light Lb while the orientation of the scanning mirror 30 is controlled. The scattered light SbB scattered at each of the parts scanned with the outgoing light Lb and the coherent light Kb are respectively converted into electric signals. The control section 3 receives the electric signals respectively from the light receiving devices 60b and 60a, and based on the received electric signals, displays a measured image, which is the result of the measurement on the diagnostic target site 100, on the display device 2.

This will be described in more detail. Among the results obtained by the scanning performed with the outgoing light Lb, the electric signal obtained as a result of the conversion from the scattered light SbB is used to generate three-dimensional shape information of the diagnostic target site 100. The electric signal obtained as a result of the conversion from the coherent light Kb is used to generate inside information of the diagnostic target site 100. The three-dimensional shape information and the inside information are displayed on the display device 2.

As described above, the dental optical measuring device 1 directs the outgoing light Lb from the handpiece 10 toward the diagnostic target site 100 and thus can generate three-dimensional volume data, which is a result of synthesis of the three-dimensional shape information and the inside information of the diagnostic target site 100. Therefore, the dental optical measuring device 1 can acquire both of the optical coherence tomography information and the three-dimensional shape information with a compact structure with no need of device replacement.

This will be described in more detail. The display device 2, the control device 3, the scanning mirror 30, the light transmission/receiving path 40 and the entering/exiting opening 50 are shared by the OCT measuring mechanism A and the surface shape measuring mechanism B as the display device 2a/2b, the control device 3a/3b, the scanning mirror 30a/30b, the light transmission/receiving path 40A/40B, and the entering/exiting opening 50a/50b. Owing to this, as compared with the case where a device for acquiring the optical coherence tomography information and a device for acquiring the three-dimensional shape information are separately prepared, the dental optical measuring device 1 can be made more compact.

At least the scanning mirror 30, the light transmission/receiving path 40 and the entering/exiting opening 50 are included in the handpiece 10 operable to make a diagnosis on the diagnostic target site 100. Owing to this, both of the optical coherence tomography information and the three-dimensional shape information can be acquired by the handpiece 10 with no need of device replacement.

Namely, one dental optical measuring device 1 can acquire highly precise three-dimensional volume data including the information on the surface and the inside of the diagnostic target site, in which the inside information on the diagnostic target site based on the optical coherence tomography information and the surface information on the diagnostic target site based on the three-dimensional surface shape information are complemented by each other. From this data, only the surface data can be extracted and used as impression data. The inside data is usable for a highly precise diagnosis on initial dental caries, root fracture or the like. The inside data is also usable for designing an upper structure for embedding an implant and implantation simulation.

The light transmission/receiving path 40 for guiding the outgoing light Lb from the scanning mirror 30 to the entering/exiting opening 50 and for guiding the scattered light Lb incident on the entering/exiting opening 50 includes the objective lenses 40L. These optical paths guide light more stably as compared with an optical path formed of, for example, a light guide or the like. The refractive index, the light guide ratio and the like of the lens can be set to provide a prescribed level of performance.

The surface shape measuring mechanism B scans and irradiates the diagnostic target site 100 with the surface measuring light LbB and receives the scattered light SbB, obtained as a result of the surface measuring light LbB directed toward the diagnostic target site 100 being scattered rearward, in an oblique direction, and thus acquires three-dimensional shape information of the surface of the diagnostic target site 100 by triangulation. The surface shape measuring mechanism B guides the light through the surface measuring light receiving parts 40b (40b1, 40b2) which are eccentric from the center of the objective lenses 40L, and thus can acquire accurate three-dimensional shape information.

The light source 20b of the surface shape measuring mechanism B and the light source 20a of the OCT measuring mechanism A are separately provided. Owing to this, the irradiation measuring light LbA2 and the surface measuring light LbB suitable for the respective types of measurement can be emitted for the measurement. Since the light source 20b of the surface shape measuring mechanism B and the light source 20a of the OCT measuring mechanism A are separately provided, the irradiation measuring light LbA2 and the surface measuring light LbB can be emitted by the light sources 20a and 20b at the same time, and thus the optical coherence tomography information and the three-dimensional shape information can be acquired at the same time.

The light dividing/interfering section 70 divides the OCT measuring light LbA into the irradiation measuring light LbA2 and the reference light LbA1 and also causes interference of the reflected light RbA and the scattered light SbA to generate the coherent light Kb. Therefore, as compared with the case where a light dividing section for dividing the OCT measuring light LbA and a light interfering section for generating the coherent light Kb are separately provided, the dental optical measuring device 1 can be made more compact.

In the above description, the scanning mirror 30, the light transmission/receiving path 40, the entering/exiting opening 50 and the light receiving device 60b are included in the handpiece 10 of the dental measuring device 1, and the scanning mirror 30, the light transmission/receiving path 40, the entering/exiting opening 50 are shared by the OCT measuring mechanism A and the surface shape measuring mechanism B. Alternatively, as long as the length of the optical path from the light dividing/interfering section 70 to the reflective mirror 72 can be set to be equal to the length of the optical path from the light dividing/interfering section 70 to the diagnostic target site 100 via the scanning mirror 30 and the light transmission/receiving path 40, the handpiece 10 may include the light dividing/interfering section 70, the light transmission/receiving path 71 and the reflective mirror 72 in addition to the scanning mirror 30, the light transmission/receiving path 40, the entering/exiting opening 50 and the light receiving device 60b, or may further include the light sources 20 in addition to the above-described elements, as represented by a plurality of one-dot chain lines in FIG. 1. The handpiece 10 may still further include the light receiving device 60a in addition to the above-described elements. Alternatively, the light receiving device 60b may be located outside the handpiece 10.

For example, the handpiece 10 may include the scanning mirror 30, the light dividing/interfering section 70, the light transmission/receiving path 40, the entering/exiting opening 50, the reflective mirror 72, and the light receiving device 60a of the OCT measuring mechanism A. Owing to this, the OCT measuring light LbA guided by the scanning mirror 30 can be divided by the light dividing/interfering section 70 and directed toward the diagnostic target site 100 via the light transmission/receiving path 40 and the entering/exiting opening 50, and also the reflected light RbA can be acquired from the reference light LbA1 directed toward by the reflective mirror 72. Interference of both of these light components is caused by the light dividing/interfering section 70, and the generated coherent light Kb is received by the light receiving device 60a. Thus, the dental optical measuring device 1 can acquire the optical coherence tomography information and also can be more compact and have higher precision.

Figure 6A:
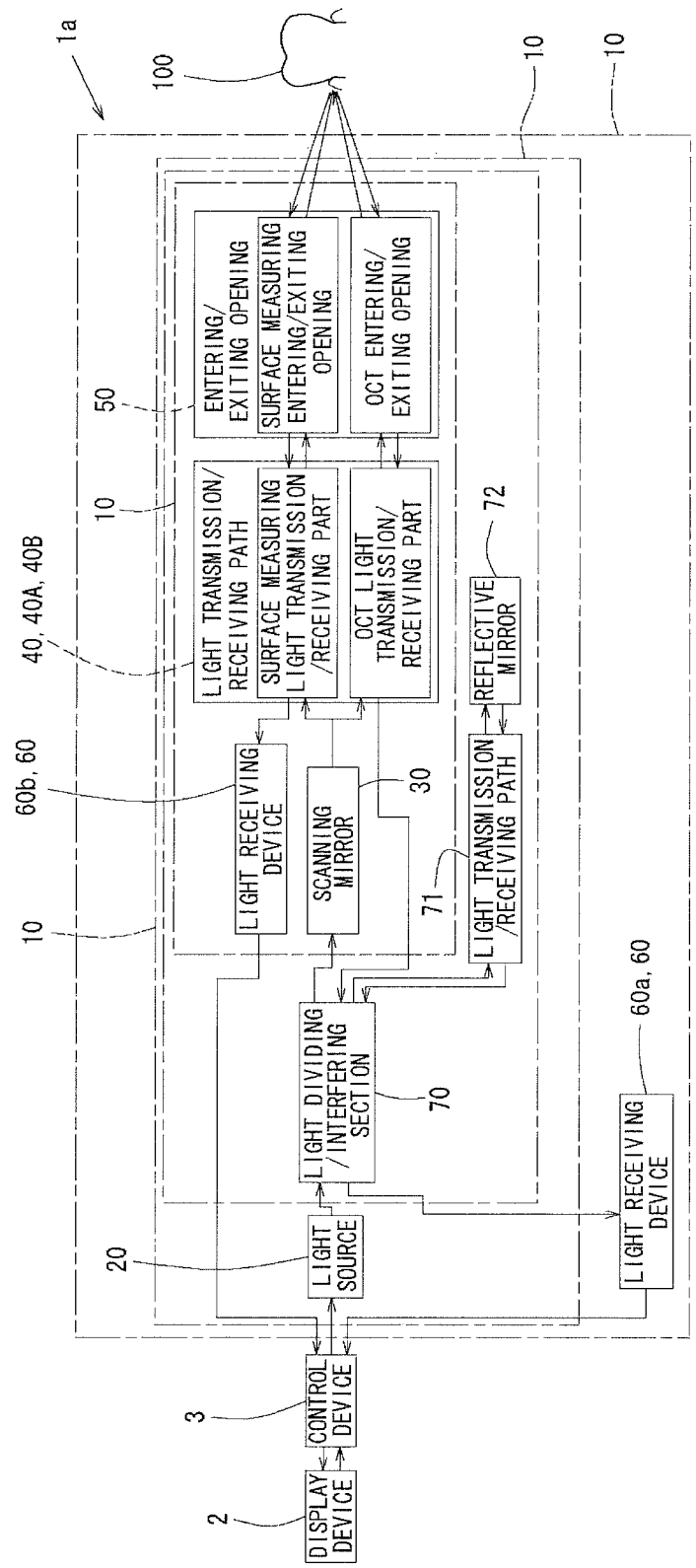
FIGS. 6A-6C show schematic structures of dental optical measuring devices in other embodiments.

FIG. 6A is a schematic structural view of a dental optical measuring device 1a in another embodiment. As shown in FIG. 6A, in the dental optical measuring device 1a, unlike in the dental optical measuring device 1, one light source 20 is shared by the OCT measuring mechanism A and the surface shape measuring mechanism B. In this structure, the light dividing/interfering section 70 divides the outgoing light Lb emitted by the light source 20 into the reference light LbA1 and the irradiation measuring light LbA2, and the OCT measuring mechanism A and the surface shape measuring mechanism B both use the irradiation measuring light LbA2 for the measurement. The light source 20 emits the outgoing light Lb having a wavelength suitable for both of the measurement performed by the OCT measuring mechanism A and the measurement performed by the surface shape measuring mechanism B.

In the dental optical measuring device 1a also, the handpiece 10 may include the scanning mirror 30, the light transmission/receiving path 40 and the entering/exiting opening 50. Alternatively, the handpiece 10 may have any of various other structures, for example, may include the light dividing/interfering section 70, the light transmission/receiving path 71 and the reflective mirror 72 in addition to the scanning mirror 30, the light transmission/receiving path 40, and the entering/exiting opening 50, may further include the light source 20 in addition to these elements, or may still further include the light receiving device 60 in addition to these elements. In the dental optical measuring device 1a also, it is necessary to set the length of the optical path from the light dividing/interfering section 70 to the reflective mirror 72 to be equal to the length of the optical path from the light dividing/interfering section 70 to the diagnostic target site 100.

Like the dental optical measuring device 1, the dental optical measuring device 1a has some of the elements shared by the OCT measuring mechanism A and the surface shape measuring mechanism B and has a part of such elements included in the handpiece 10. Owing to this, the dental optical measuring device 1a provides the same effect as that of the dental optical measuring device 1. In addition, the dental optical measuring device 1a has a larger number of elements shared by the mechanisms A and B than the dental optical measuring device 1, and therefore provides a larger effect.

Figure 6B:
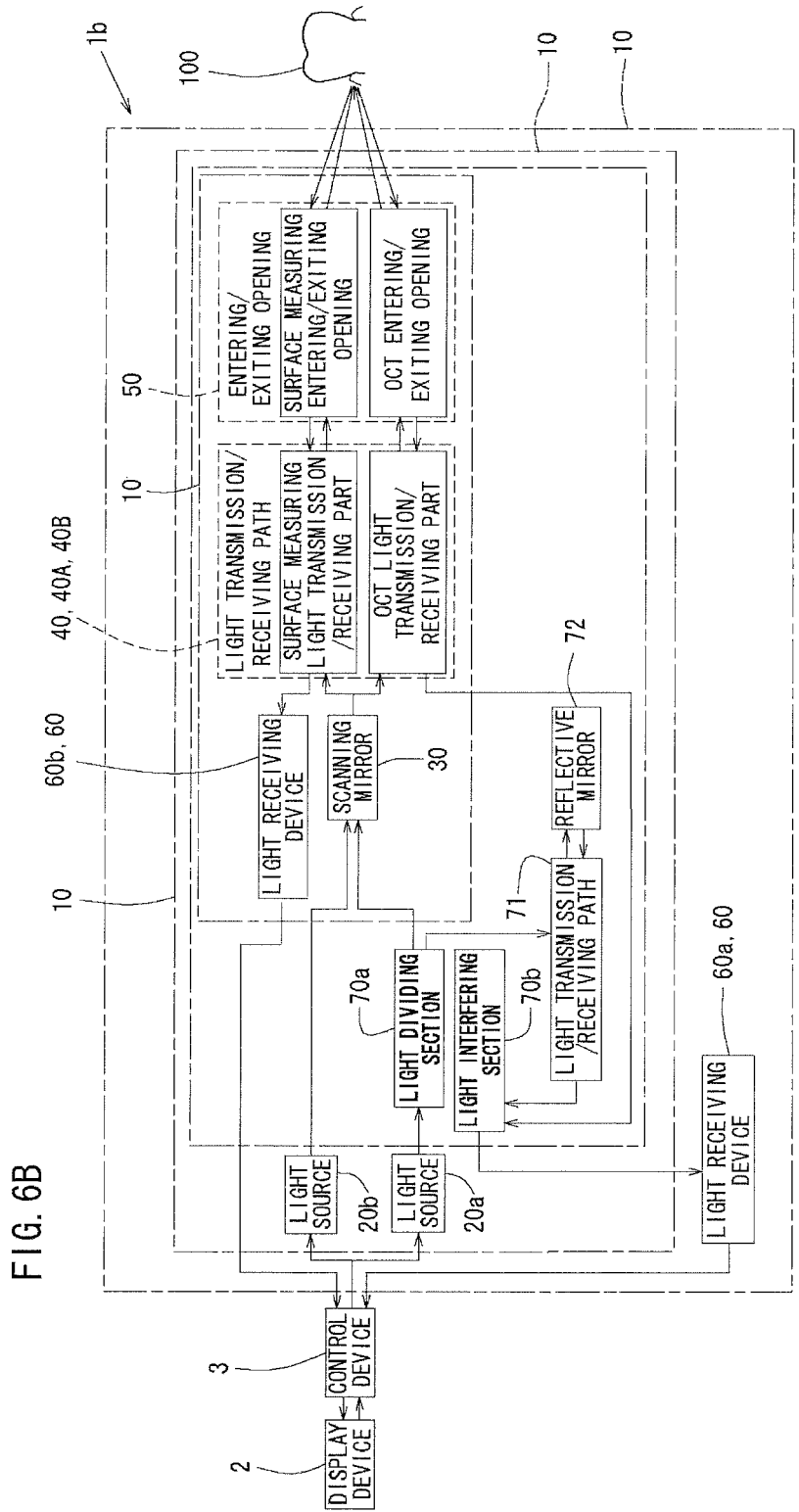

FIG. 6B is a schematic structural view of a dental optical measuring device 1b in still another embodiment. As shown in FIG. 6B, in the dental optical measuring device 1b, unlike in the dental optical measuring device 1 including the light dividing/interfering section 70, a light dividing section 70a for dividing the OCT measuring light LbA into the reference light LbA1 and the irradiation measuring light LbA2, and a light interfering section 70b for causing interference of the reflected light RbA and the scattered light SbA to the generate the coherent light Kb, are separately provided.

In this structure, the outgoing light Lb emitted by the light source 20 is divided into the reference light LbA1 and the irradiation measuring light LbA2 by the light dividing section 70a, and the reference light LbA1 is directed toward the reflective mirror 72 via the light transmission/receiving path 71. The reflected light RbA reflected by the reflective mirror 72 is guided to the light interfering section 70b via the light transmission/receiving path 71. The scattered light SbA guided through the light transmission/receiving path 40 is also guided to the light interfering section 70b. The light interfering section 70b causes interference of the reflected light RbA and the scattered light SbA to generate the coherent light Kb, and the coherent light Kb is guided to the light receiving device 60a.

In the case of the dental optical measuring device 1b, the length of the optical path from the light dividing section 70a to the diagnostic target site 100 is set to be equal to the length of the optical path from the light dividing section 70a to the reflective mirror 72, and the length of the optical path from the diagnostic target site 100 to the light interfering section 70b is set to be equal to the length of the optical path from the reflective mirror 72 to the light interfering section 70b.

Like the dental optical measuring device 1, the dental optical measuring device 1b has some of the elements shared by the OCT measuring mechanism A and the surface shape measuring mechanism B. Owing to this, the dental optical measuring device 1b provides the same effect as that of the dental optical measuring device 1.

Like in the dental optical measuring device 1, in the dental optical measuring device 1b also, the scanning mirror 30, the light transmission/receiving path 40, the entering/exiting opening 50 and the light receiving device 60b are included in the handpiece 10, and the scanning mirror 30, the light transmission/receiving path 40, the entering/exiting opening 50 are shared by the OCT measuring mechanism A and the surface shape measuring mechanism B. Alternatively, as long as the length of the optical path from the light dividing section 70a to the reflective mirror 72 can be set to be equal to the length of the optical path from the light dividing section 70a to the diagnostic target site 100 via the scanning mirror 30 and the light transmission/receiving path 40 and the length of the optical path from the diagnostic target site 100 to the light interfering section 70b via the scanning mirror 30 and the light transmission/receiving path 40 can be set to be equal to the length of the optical path from the reflective mirror 72 to the light interfering section 70b, the handpiece 10 may include the light dividing section 70a, the light interfering section 70b, the light transmission/receiving path 71 and the reflective mirror 72 in addition to the scanning mirror 30, the light transmission/receiving path 40, the entering/exiting opening 50 and the light receiving device 60b, or may further include the light source 20 in addition to the above-described elements, the light transmission/receiving path 71 and the reflective mirror 72. The handpiece 10 may still further include the light receiving device 60a in addition to the above-described elements. Alternatively, the light receiving device 60b may be located outside the handpiece 10.

Figure 6C:
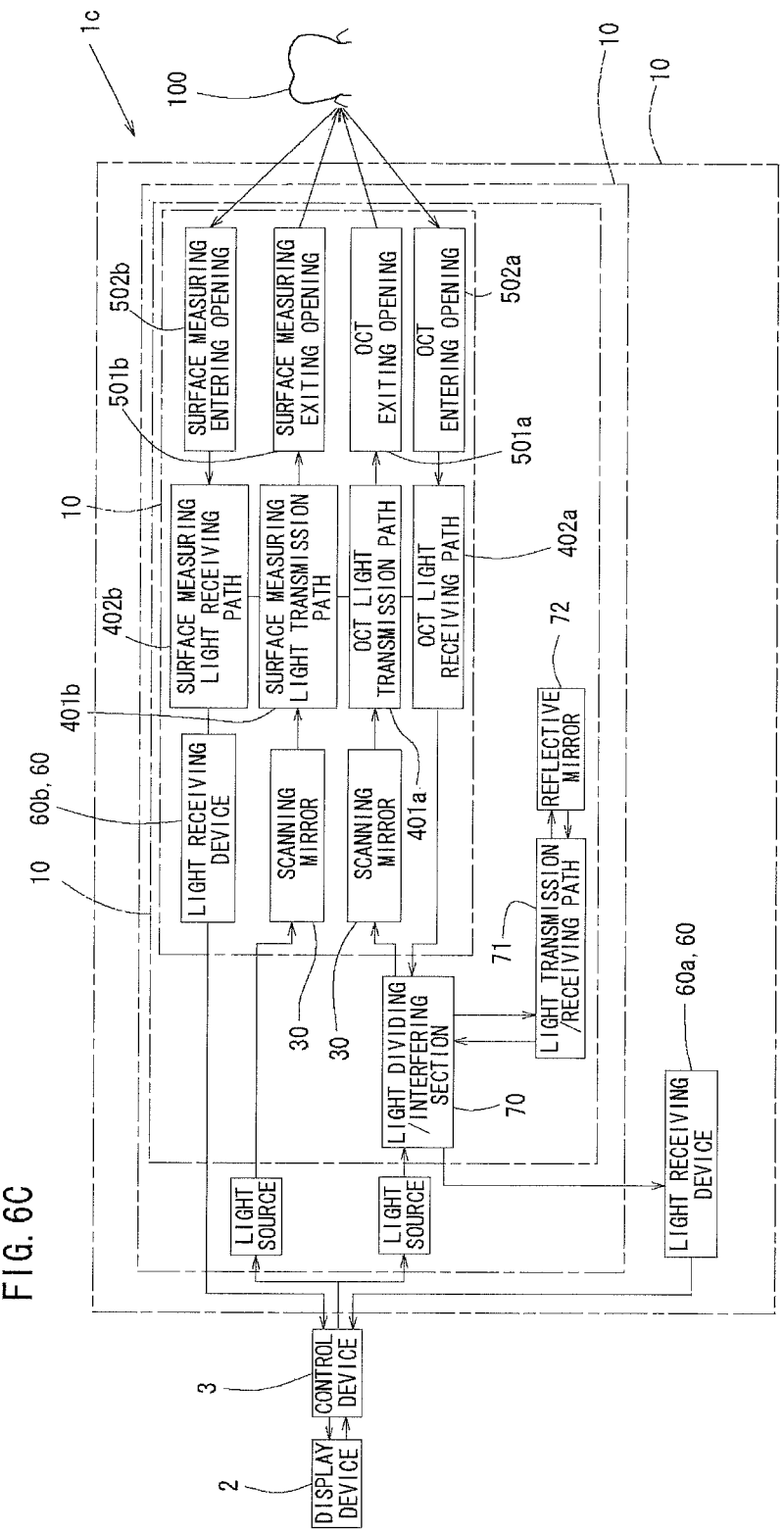

FIG. 6C is a schematic structural view of a dental optical measuring device 1c in still another embodiment. As shown in FIG. 6C, in the dental optical measuring device 1c, only the display device 2 and the control device 3 are shared by the OCT measuring mechanism A and the surface shape measuring mechanism B, and the other elements are provided separately for the OCT measuring mechanism A and the surface shape measuring mechanism B. In the dental optical measuring device 1, the light transmission/receiving path 40 acts both as a light transmission path for guiding the outgoing light Lb and a light receiving path for guiding the scattered light Sb. By contrast, in the dental optical measuring device 1c, light transmission paths 401 (401a, 401b), light receiving paths 402 (402a, 402b), exiting openings 501 (501a, 501b) and entering opening 502 (502a, 502b) are separately provided for the OCT measuring mechanism A and the surface shape measuring mechanism B.

The surface shape measuring mechanism B performs surface measurement on the diagnostic target site 100 by triangulation. The light receiving path 402b of the surface shape measuring mechanism B is located at a position which is eccentric from the center or the vicinity thereof of the handpiece 10 such that the scattered light SbB obtained from the surface measuring light LbB directed toward the diagnostic target site 100 is incident on the handpiece 10 in an oblique direction.

The dental optical measuring device 1c structured as described above can also acquire the inside information based on the optical coherence tomography information acquired by the OCT measuring mechanism A and the three-dimensional shape information acquired by the surface shape measuring mechanism B with no need of device replacement, by inserting the handpiece 10 into the oral cavity.

Since the light source 20a and the light source 20b are separately provided, the OCT measuring mechanism A and the surface shape measuring mechanism B can use the outgoing light LbB of a wavelength suitable for the respective measurement.

Like in the dental optical measuring device 1, in the dental optical measuring device 1c also, the scanning mirrors 30, the light transmission paths 401, the light receiving paths 402, the exiting openings 501, the entering openings 502 and the light receiving device 60b are included in the handpiece 10. Alternatively, as long as the length of the optical path from the light dividing/interfering section 70 to the reflective mirror 72 can be set to be equal to the length of the optical path from the light dividing/interfering section 70 to the diagnostic target site 100 via the scanning mirror 30, the light transmission path 401a and the exiting opening 501a and the length of the optical path from the reflective mirror 72 to the light dividing/interfering section 70 can be set to be equal to the length of the optical path from the diagnostic target site 100 to the light dividing/interfering section 70 via the entering opening 502a, the light receiving path 402a and the scanning mirror 30, the handpiece 10 may include the light dividing/interfering section 70, the light transmission/receiving path 71 and the reflective mirror 72 in addition to the scanning mirrors 30, the light transmission paths 401, the light receiving paths 402, the exiting openings 501, the entering openings 502 and the light receiving device 60b, or may further include the light sources 20 in addition to the above-described elements. The handpiece 10 may still further include the light receiving device 60a in addition to the above-described elements. Alternatively, the light receiving device 60b may be located outside the handpiece 10.

In the above description, the measuring mechanism A is of SS-OCT (swept source OCT). The SS-OCT measuring mechanism A operates as follows. Wavelength scanning laser light is used as the OCT measuring light LbA. The OCT measuring light LbA is divided by the light dividing/interfering section 70 into the irradiation measuring light LbA2 and the reference light LbA1. The irradiation measuring light LbA2 is directed toward the diagnostic target site 100. Interference of the reflected light RbA reflected by the reflective mirror 72 having a fixed optical path length to the light dividing/interfering section 70 and the scattered light SbA scattered rearward by the diagnostic target site 100 is caused to generate the coherent light Kb. Components of coherent light Kb at various wavelengths are acquired from the length scanning laser light, converted into electric signals, and processed by Fourier transformation. Thus, the optical coherence tomography information is acquired. Alternatively, the measuring mechanism A may be of TD-OCT (time domain OCT) or SD-OCT (spectral domain OCT).

The TD-OCT measuring mechanism A operates as follows, for example. Low-coherence light from a super-luminescent diode is used as the OCT measuring light LbA. The OCT measuring light LbA is divided by the light dividing/interfering section 70 into the irradiation measuring light LbA2 and the reference light LbA1. The irradiation measuring light LbA2 is directed toward the diagnostic target site 100. Interference of the reflected light RbA reflected by the reflective mirror 72 having a moving unit for changing the optical path length to the light dividing/interfering section 70 and the scattered light SbA scattered rearward by the diagnostic target site 100 is caused to generate the coherent light Kb. The reflective mirror 72 is moved to acquire components of coherent light Kb at positions of various optical path lengths and converted into electric signals. Thus, the optical coherence tomography information is acquired.

In the case of the SD-OCT measuring mechanism A operates as follows, for example. Low-coherence light from a super-luminescent diode is used as the OCT measuring light LbA. The OCT measuring light LbA is divided by the light dividing/interfering section 70 into the irradiation measuring light LbA2 and the reference light LbA1. The irradiation measuring light LbA2 is directed toward the diagnostic target site 100. Interference of the reflected light RbA reflected by the reflective mirror 72 having a fixed optical path length to the light dividing/interfering section 70 and the scattered light SbA scattered rearward by the diagnostic target site 100 is caused to generate the coherent light Kb. Coherent light components at various wavelengths are acquired by use of a spectroscope, converted into electric signals, and processed by Fourier transformation. Thus, the optical coherence tomography information is acquired.

The OCT measuring mechanism A may be of SS-OCT, TD-OCT or SD-OCT. Any method of the OCT measuring mechanism A suitable for the diagnostic target site 100, the facility environment or the like is usable.

The surface shape measuring mechanism B using triangulation described above may use any of a spot light projection method (light probe method), a light section method (slit light projection method), a pattern light projection method, a space coding method and a phase shift method.

This will be described in more detail. The surface shape measuring mechanism B using the spot light projection method (light probe method) operates as follows, for example. Laser light is used as the surface measuring light LbB. The surface measuring light LbB is reflected by the scanning mirror 30 and directed toward the diagnostic target site 100. Scattered light SbB scattered rearward by the diagnostic target site 100 is captured by a CCD (Charge Coupled Device) camera, a CMOS (Complementary Metal Oxide Semiconductor) camera or the like in a direction having an angle called "triangulation angle" with respect to the optical axis of the laser light directed toward the diagnostic target site 100. Thus, a three-dimensional position in the diagnostic target site 100 is acquired by triangulation. The orientation of the scanning mirror 30 is varied to acquire three-dimensional shape information of the entirety of the diagnostic target site 100.

The surface shape measuring mechanism B using the light section method (slit light projection method) operates as follows, for example. Line light, which is generated by causing white light or the like to pass a slit, using laser light for scanning, or causing laser light to pass a cylindrical lens, is used as the surface measuring light LbB. The surface measuring light LbB is reflected by the scanning mirror 30 and directed toward the diagnostic target site 100. Scattered light SbB scattered rearward by the diagnostic target site 100 is captured by a CCD camera, a CMOS camera or the like in a direction having the triangulation angle with respect to the optical axis of the line light directed toward the diagnostic target site 100. Thus, a three-dimensional position in the diagnostic target site 100 is acquired by triangulation. The orientation of the scanning mirror 30 is varied to acquire three-dimensional shape information of the entirety of the diagnostic target site 100.

The surface shape measuring mechanism B using the pattern light projection method operates as follows, for example. Pattern light is projected toward the diagnostic target site 100. Scattered light SbB scattered rearward by the diagnostic target site 100 is captured by a CCD camera, a CMOS camera or the like in a direction having the triangulation angle with respect to the optical axis of the pattern light directed toward the diagnostic target site 100. Thus, three-dimensional shape information of the entirety of the diagnostic target site 100 is acquired.

The surface shape measuring mechanism B using the space coding method or the phase shift method operates as follows. A plurality of stripe patterns of light are projected toward the diagnostic target site 100 sequentially. Scattered light SbB scattered rearward by the diagnostic target site 100 is captured by a CCD camera, a CMOS camera or the like in a direction having the triangulation angle with respect to the optical axis of the pattern light directed toward the diagnostic target site 100. Thus, three-dimensional shape information of the entirety of the diagnostic target site 100 is acquired.

The surface shape measuring mechanism B may use the triangulation of any of the spot light projection method (light probe method), the light section method (slit light projection method), the pattern light projection method, the space coding method and the phase shift method. Any method of the surface shape measuring mechanism B suitable for the diagnostic target site 100, the facility environment or the like is usable.

Figure 7:
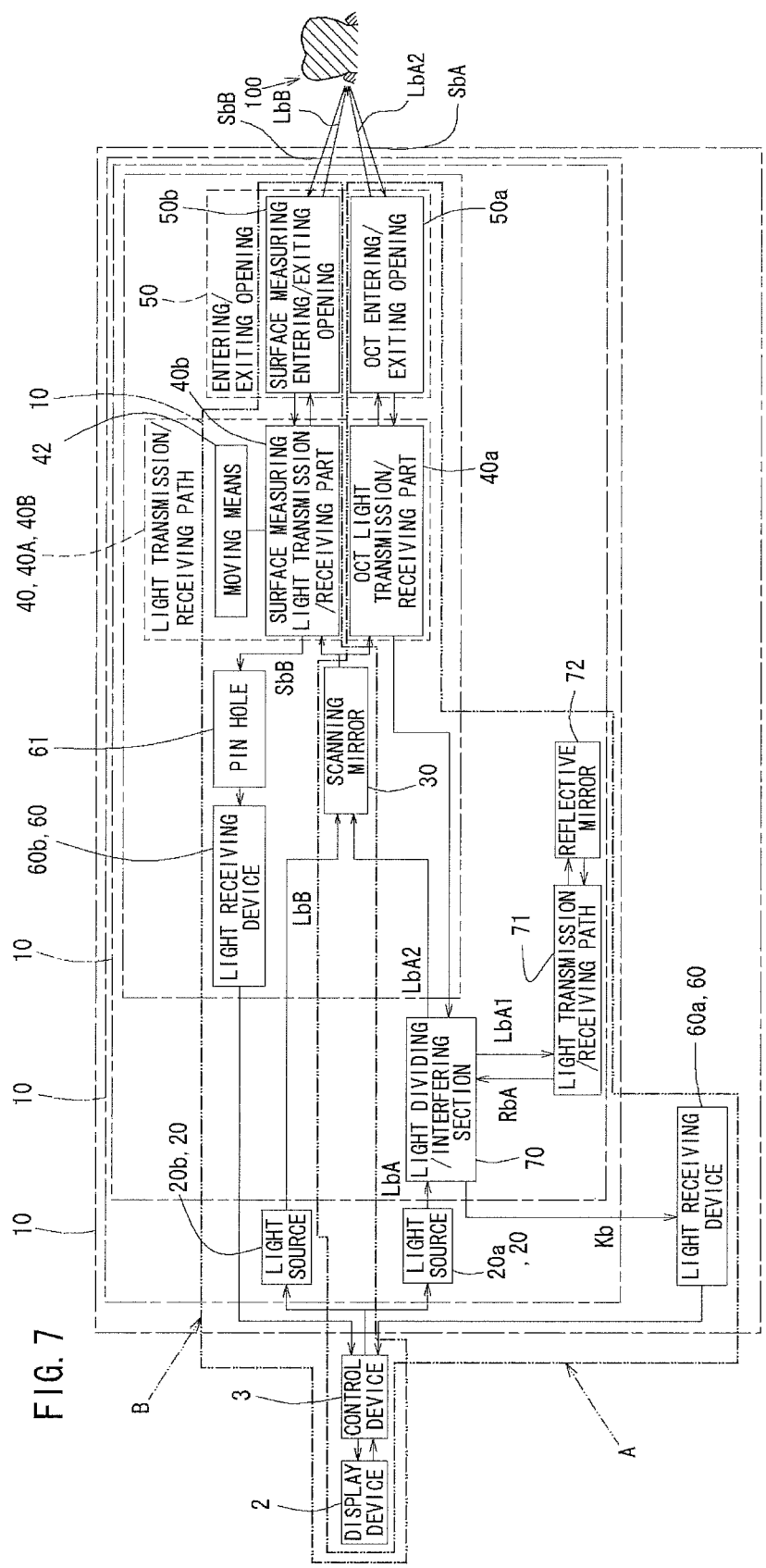
FIG. 7 is a schematic structural view of a dental optical measuring device in still another embodiment.

The surface shape measuring mechanism B may use a method other than triangulation; for example, a confocal method. In the case of the surface shape measuring mechanism B using the confocal method, the structure as shown in FIG. 7 is provided. In addition to the elements of the surface shape measuring mechanism B using triangulation, a moving unit 42 for moving the surface measuring light transmission/receiving part 40b and a pinhole 61 for allowing the scattered light SbB to pass therethrough are located upstream with respect to the light receiving device 60b.

The surface shape measuring mechanism B using the confocal method operates as follows, for example. Laser light is used as the surface measuring light LbB. The surface measuring light LbB is reflected by the scanning mirror 30, passes the objective lenses 40L having the moving unit 42 for moving the objective lenses 40L in a direction of the optical axis thereof, and is directed toward the diagnostic target site 100. As shown in FIG. 3B, the scattered light SbB scattered rearward in the same direction as that of the optical axis of the surface measuring light LbB directed toward the diagnostic target site 100 is collected on the pin hole 61, and is detected by, for example, a photodiode or a photomultiplier tube. The scattered light SbB from a position other than the focal point of the objective lenses 40L is cut by the pin hole 61, and the objective lenses 40L are moved by the moving unit 42 in the direction of the optical axis thereof. Thus, the position of a surface of an object, which is the diagnostic target site 100, can be detected. By performing scanning by use of the scanning mirror 30, three-dimensional surface information of the diagnostic target site 100 is acquired.

In the case where the light transmission/receiving path 40 is moved together with the OCT light transmission/receiving part 40a as well as the surface measuring light transmission/receiving part 40b by the moving unit 42, it is necessary that the length of the optical path from the light dividing/interfering section 70 to which the reference light LbA1 is to be guided to the reflective mirror 72 is set to be equal to the length of the optical path of the irradiation measuring light LbA2 from the light dividing/interfering section 70 to the diagnostic target site 100 via the scanning mirror 30, the light transmission/receiving path 40 and the entering/exiting opening 50. Therefore, a moving unit for moving the reflective mirror 72 in synchronization with the movement of the light transmission/receiving path 40 by the moving unit 42 is provided.

The surface measurement may also be performed by a TOF (Time of Flight) method, by which the time required for returning the scattered light SbB scattered by the diagnostic target site 100. Alternatively, the surface measurement may be performed by a focal point method, by which an image of the diagnostic target site 100 is acquired and the focal position is measured.

In the above description, the scanning mirror is provided as an element of the dental optical measuring device. The dental optical measuring device may include one scanning mirror performing two-axial scanning, or two scanning mirrors each performing monoaxial scanning. In the case where the scanning mirror is shared by the OCT measuring mechanism and the surface shape measuring mechanism, one scanning mirror performing two-axial scanning may be shared, or two scanning mirrors each performing monoaxial scanning may be shared. Alternatively, one scanning mirror performing monoaxial scanning may be shared, while one scanning mirror performing monoaxial scanning is provided for the OCT measuring mechanism and another scanning mirror performing monoaxial scanning is provided for the surface shape measuring mechanism.

In the case where the scanning mirror is not shared by the OCT measuring mechanism and the surface shape measuring mechanism, two scanning mirrors each performing two-axial scanning may be provided, or four scanning mirrors each performing monoaxial scanning may be provided. The scanning mirror performing two-axial scanning may be, for example, a MEMS (Micro Electro Mechanical Systems) mirror. The scanning mirror performing monoaxial scanning may be, for example, a MEMS mirror, a galvano mirror or the like.

The measurement result display section of the present invention corresponds to the display device 2, 2a, 2b of the embodiments; and similarly, the measurement control section corresponds to the control device 3, 3a, 3b;

the measuring light corresponds to the outgoing light Lb, the irradiation measuring light LbA2, the surface measuring light LbB;

the measuring light emitting section corresponds to the light source 20, 20a, 20b;

the measurement target corresponds to the diagnostic target site 100 including the tooth 101 and the gum 102;

the exiting opening and entering opening correspond to the entering/exiting opening 50, 50a, 50b;

the light transmission path and the light receiving path correspond to the light transmission/receiving path 40, 40A, 40B;

the light receiving section corresponds to the light receiving device 60, 60a, 60b;

the optical three-dimensional surface measuring system structure corresponds to the surface shape measuring mechanism B;

the light dividing section corresponds to the light dividing section 70a;

the light interfering section corresponds to the light interfering section 70b;

the light dividing section, and the light interfering section and the light dividing section, correspond to the light dividing/interfering section 70;

the reflected reference light corresponds to the reflected light RbA;

the coherent light receiving section corresponds to the light receiving device 60a;

the optical coherence tomography measuring system structure corresponds to the OCT measuring mechanism A;

the diagnosing tool corresponds to the handpiece 10;

the lens system light guide path corresponds to the light transmission/receiving path 40;

the optical axis corresponds to the OCT light transmission/receiving part 40a;

the scattered light corresponds to the scattered light SbA reflected or scattered on the surface of, and inside of, the diagnostic target site 100, the scattered light SbB reflected or scattered on the surface of, and inside of, the diagnostic target site 100; and the eccentric position corresponds to the surface measuring light transmission/receiving part 40b.

However, the present invention is not limited to the above-described embodiments, and may be implemented in many other embodiments.

For example, in the above description, the OCT measuring mechanism A is of a Fourier domain system. Alternatively, the OCT measuring mechanism A may be of a time domain system.

INDUSTRIAL APPLICABILITY

The present invention is usable for various optical measuring devices for acquiring both of optical coherence tomography information and three-dimensional shape information of a living organism by use of laser light to perform, for example, impression taking.

DESCRIPTION OF THE REFERENCE NUMERALS

1 . . . Dental optical measuring device
2, 2a, 2b . . . Display device
3, 3a, 3b . . . Control device
10 . . . Handpiece
20, 20a, 20b . . . Light source
30, 30a, 30b . . . Scanning mirror
40, 40A, 40B . . . Light transmission/receiving path
50 . . . Entering/exiting opening
50a . . . OCT entering/exiting opening
50b . . . Surface measuring entering/exiting opening
60, 60a, 60b . . . Light receiving device
70 . . . Light dividing/interfering section
70a . . . Light dividing section
70b . . . Light interfering section
72 . . . Reflective mirror
100 . . . Diagnostic target site
101 . . . Tooth
102 . . . Gum
Kb . . . Coherent light
Lb . . . Outgoing light
LbA . . . OCT measuring light
LbA1 . . . Reference light
LbA2 . . . Irradiation measuring light
LbB . . . Surface measuring light
RbA . . . Reflected light
Sb, SbA, SbB . . . Scattered light
A . . . OCT measuring mechanism
B . . . Surface shape measuring mechanism

What is claimed is:

1. A dental optical scanning device, comprising:
an optical three-dimensional surface scanning system structure including a scan result display section for displaying at least a scan result, a scan control section for controlling a scan, a scanning light emitting section for emitting scanning light, a scanning mirror usable for scanning performed with the scanning light, an exiting opening through which the scanning light is directed toward a scan target, a light transmission path for guiding the scanning light to the exiting opening, an entering opening on which the scanning light directed from the exiting opening is incident after being scattered by the scan target, a light receiving path for guiding the scattered light incident on the entering opening, and a light receiving section for receiving the scattered light guided by the light receiving path; and an optical coherence tomography scanning system structure including a scan result display section for displaying at least a scan result, a scan control section for controlling a scan, a scanning light emitting section for emitting scanning light, a light dividing section for dividing the scanning light into scanning light and reference light, a scanning mirror usable for scanning performed with the scanning light, an exiting opening through which the scanning light is directed toward the scan target, a light transmission path for guiding the scanning light to the exiting opening, an entering opening on which the scanning light directed from the exiting opening is incident after being scattered by the scan target, a light receiving path for guiding the scattered light incident on the entering opening, a reflective mirror for reflecting the reference light obtained as a result of the division performed by the light dividing section, a light interfering section for causing interference of the reflected reference light reflected by the reflective mirror and the scattered light, and a coherent light receiving section for receiving coherent light generated by the interference performed by the light interfering section;

wherein:
the optical three-dimensional surface scanning system structure and the optical coherence tomography scanning system structure share at least one of the scan result display section, the scan control section, the scanning light emitting section, the scanning mirror, the light transmission path, the exiting opening, the entering opening, and the light receiving path; and at least the scanning mirror, the light transmission path, the exiting opening, the entering opening, and the light receiving path are included in a diagnosing tool operable to make a diagnosis on the scan target;

the light transmission path and the light receiving path include a lens system light guide path for guiding the scanning light to the exiting opening and for guiding the scattered light from the entering opening;

an entirety of the light transmission path and the light receiving path of the optical three-dimensional surface scanning system structure are located at an eccentric position which is eccentric from the center of the lens system light guide path; and the light transmission path and the light receiving path of the optical coherence tomography scanning system structure are located at the center of the lens system light guide path.

2. A dental optical scanning device according to claim 1, wherein the optical three-dimensional surface scanning system structure and the optical coherence tomography scanning system structure share the scanning mirror, the light transmission path, the exiting opening, the entering opening, and the light receiving path.

3. A dental optical scanning device according to claim 1, wherein:
the scanning light emitting section of the optical three-dimensional surface scanning system structure and the scanning light emitting section of the optical coherence tomography scanning system structure are separately provided.

4. A dental optical scanning device according to claim 1, wherein the light dividing section and the light interfering section are integrally provided as a light dividing/interfering section for dividing the scanning light into the scanning light and the reference light and causing interference of the reflected reference light and the scattered light to generate coherent light.

5. A dental optical scanning device according to claim 4, wherein the scanning mirror, the light dividing/interfering section, the light transmission path, the exiting opening, the light receiving path, the reflective mirror, the coherent light receiving section and the entering opening of the optical coherence tomography scanning system structure are included in the diagnosing tool.

6. A dental optical scanning diagnosing tool usable to make a diagnosis performed by use of scanning light directed toward a scan target, the dental optical scanning diagnosing tool comprising:

an optical three-dimensional surface scanning system structure including a scanning light emitting section for emitting scanning light, a scanning mirror usable for scanning performed with the scanning light, an exiting opening through which the scanning light is directed toward the scan target, a light transmission path for guiding the scanning light to the exiting opening, an entering opening on which the scanning light directed from the exiting opening is incident after being scattered by the scan target, a light receiving path for guiding the scattered light incident on the entering opening, and a light receiving section for receiving the scattered light guided by the light receiving path; and an optical coherence tomography scanning system structure including a scanning light emitting section for emitting scanning light, a light dividing section for dividing the scanning light into scanning light and reference light, a scanning mirror usable for scanning performed with the scanning light, an exiting opening through which the scanning light is directed toward the scan target, a light transmission path for guiding the scanning light to the exiting opening, a light receiving path for guiding scattered light obtained as a result of the scanning light directed from the exiting opening being scattered by the scan target and incident on the entering opening, a reflective mirror for reflecting the reference light obtained as a result of the division performed by the light dividing section, a light interfering section for causing interference of the reflected reference light reflected by the reflective mirror and the scattered light, and a coherent light receiving section for receiving coherent light generated by the interference performed by the light interfering section;

wherein:
at least the scanning mirrors, the light transmission paths, the exiting openings, the entering openings, and the light receiving paths are included in a tool main body operable to make a diagnosis on the scan target;

the optical three-dimensional surface scanning system structure and the optical coherence tomography scanning system structure share at least one of the scan result display section, the scan control section, the scanning light emitting section, the scanning mirror, the light transmission path, the exiting opening, the entering opening, and the light receiving path;

the light transmission path and the light receiving path include a lens system light guide path for guiding the scanning light to the exiting opening and for guiding the scattered light from the entering opening;

an entirety of the light transmission path and the light receiving path of the optical three-dimensional surface scanning system structure are located at an eccentric position which is eccentric from the center of the lens system light guide path; and the light transmission path and the light receiving path of the optical coherence tomography scanning system structure are located at the center of the lens system light guide path.

7. A dental optical scanning diagnosing tool according to claim 6, wherein the optical three-dimensional surface scanning system structure and the optical coherence tomography scanning system structure share the scanning mirror, the light transmission path, the exiting opening, the entering opening, and the light receiving path.

8. A dental optical scanning diagnosing tool according to claim 6, wherein the light dividing section and the light interfering section are integrally provided as a light dividing/interfering section for dividing the scanning light into the scanning light and the reference light and causing interference of the reflected reference light and the scattered light to generate coherent light.

9. A dental optical scanning diagnosing tool according to claim 8, wherein the scanning mirror, the light dividing/interfering section, the light transmission path, the exiting opening, the light receiving path, the reflective mirror, the coherent light receiving section, and the entering opening of the optical coherence tomography scanning system structure are included in the main body of the tool main body.

10. A dental optical scanning device according to claim 2, wherein the light transmission path and the light receiving path include a lens system light guide path for guiding the scanning light to the exiting opening and for guiding the scattered light from the entering opening.

11. A dental optical scanning diagnosing tool according to claim 7, wherein the light transmission path and the light receiving path include a lens system light guide path for guiding the scanning light to the exiting opening and for guiding the scattered light from the entering opening.

* * * * *